United States Patent
Murata et al.

(10) Patent No.: US 6,849,597 B2
(45) Date of Patent: Feb. 1, 2005

(54) NEUROPROTECTIVE DRUG

(75) Inventors: Takahiko Murata, Kyoto (JP); Tadashi Ohyama, Kyoto (JP); Masahiro Amakawa, Kyoto (JP); Keiko Fujita, Tokyo (JP); Haruyoshi Ueo, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/169,423

(22) PCT Filed: Dec. 28, 2000

(86) PCT No.: PCT/JP00/09431

§ 371 (c)(1),
(2), (4) Date: Jun. 27, 2002

(87) PCT Pub. No.: WO01/47558

PCT Pub. Date: Jul. 5, 2001

(65) Prior Publication Data

US 2003/0100494 A1 May 29, 2003

(30) Foreign Application Priority Data

Dec. 28, 1999 (JP) .......................................... 11-375513

(51) Int. Cl.⁷ ......................... A61K 38/16; C07K 38/02

(52) U.S. Cl. ......................... 514/2; 435/325; 514/299; 930/120

(58) Field of Search .............................. 435/325; 514/2, 514/299; 930/120

(56) References Cited

FOREIGN PATENT DOCUMENTS

| WO | WO 97/24369 | 7/1997 |
| WO | WO 97/41878 | 11/1997 |
| WO | WO 99/09991 | 3/1999 |
| WO | WO 00/48623 | 8/2000 |

OTHER PUBLICATIONS

C.Y. Bowers. Cell. Mol. Life Sci. 54: 1316–1329 (1998).

Scheepens A., et al., Alterations in the neural growth hormone axis following hypoxic–ischemic brain injury, (1999) *Molecular Brain Research*, 68: 88–100.

De Gennaro Colonna V., et al., Cardiac ischemia and impairment of vascular endothelium function in hearts from growth hormone–deficient rats: protection by hexarelin, (1997) *European J. Pharm.*, 334: 201–207.

Smith, R.G., et al., A new orphan receptor involved in pulsatile growth hormone release, (1999) *Trends Endocrinol. Metab.*, 10 (4): 128–135.

Kojima, M., et al., Ghrelin is a growth–hormone–releasing acylated peptide from stomach, (1999) *Nature*, 402 (6762): 656–660.

Sonntag, W.E., et al., Decreases in cerebral microvasculature with age are associated with the decline in growth hormone and insulin–like growth factor 1, (1997) *Enodcrinology*, 138 (8): 3515–20.

*Primary Examiner*—Robert A. Wax
(74) *Attorney, Agent, or Firm*—Nixon Peabody LLP

(57) ABSTRACT

An agent for prevention or treatment of diseases involving degeneration or death of nerve cells, characterized by containing a growth hormone secretion promoting substance as an active ingredient, is provided.

14 Claims, 6 Drawing Sheets

NEUROPROTECTIVE DRUG

TECHNICAL FIELD

This invention relates to a neuroprotective drug for preventing or treating diseases involving degeneration or death of nerve cells.

BACKGROUND ART

A nerve cell constitutes one unit, called a neuron, consisting of a nerve cell body, dendrites and an axon. Neurons together form a junctional area called a synapse, and transmit sensory impulses from the periphery, or signals such as motor commands from the brain. In the brain, nerve cells form synapses complicatedly and elaborately to produce higher functions, such as mental activity, memory, speech, behavior and cognition. Degeneration or death of nerve cells impairs the function of nerve cells, and may cause disorder of higher functions.

Degeneration or death of a nerve cell is generally classified as necrosis typified by ischemic necrosis, and apoptosis which is a cellular death actively caused by the cell itself. Necrosis begins with swelling of the cell and collapse of the cytoplasm, caused by energy exhaustion due to ischemia, excitation due to influx of an excitatory amino acid or voltage-gated calcium, or damage due to a free radical. Apoptosis, on the other hand, includes delayed neuronal death which is observed several days after ischemia, or that which occurs because a substance like an abnormal protein is accumulated in the cytoplasm. Apoptosis mainly involves shrinkage of the cell, condensation of cell nuclear chromatin, and fragmentation of nuclear DNA, although details of the mechanism of apoptosis are unknown.

Many cerebral diseases involve degeneration or death of nerve cells, and they are roughly divided into those due to ischemia and those not caused by ischemia.

Of the cerebral diseases due to ischemia, cerebrovascular disorders occur most frequently, and they are classified by cause into thrombotic infarction due to arteriosclerosis of a cerebral vessel, cardio-embolic infarction, hypertensive intracerebral bleeding, and subarachnoid hemorrhage following rupture of cerebral aneurysm. As a result, these cerebrovascular disorders present with varieties of neuropsychological symptoms, such as aphasia, apraxia, agnosia, emotional or memory disturbance, and dementia. Nerve cells are very vulnerable to ischemia. Thus, when cerebral circulation is disturbed, nerve cells are damaged, resulting in necrosis of nerve cells or local necrosis (infarction) of the brain. Cerebral hemorrhage also causes ischemia due to disruption of bloodstream, or destruction of the cerebral parenchyma due to hematoma, followed by edema of surrounding tissue in the brain or disturbance of microcirculation. In subarachnoid hemorrhage as well, ischemia due to cerebrovascular spasm develops. Such cerebrovascular disorders are treated by symptomatic therapies or drug therapies suitable for the causes. These therapies include lysis of thrombus, removal of edema, and lowering of an elevated blood pressure to the normal pressure.

When restoration of the bloodstream begins after ischemia, free radicals sharply increase, and leukocytes are activated to produce cytokines. Furthermore, the endothelium, thrombocytes and blood coagulation are activated to accelerate infarction. Factors inducing such degeneration and necrosis of cells include, for example, energy reduction due to ATP depletion, cell acidosis, glutamate release, calcium ion influx, membranous phospholipid degradation and subsequent free fatty acid accumulation, and free radical generation.

In view of these factors, research and development have been performed of drugs, such as calcium channel blockers, platelet aggregation inhibitors, glutamate antagonists, CDP-amines, free radical scavengers/antioxidants, perfluorocarbons, and thrombolytic agents for improving cerebral blood flow and/or neuronal output. Many such agents for treatment of diseases associated with ischemic events of the brain have been studied and developed, but satisfactory drugs are still unavailable.

Examples of cerebral diseases not ascribed to ischemia are what we call neurodegenerative diseases in which a certain line of nerve cells fall off. Representative of them are Alzheimer disease and Parkinson disease. Cholinesterase inhibitors aimed at activation of cholinergic nerves are used for treatment of Alzheimer disease. L-DOPA has long been used as a drug for treatment of Parkinson disease. However, these drugs do not suppress the death of nerve cells.

In addition to the above-described cerebral diseases, incidents, such as trauma, infection, tumor, metabolic disorder and drug intoxication, injure nerve cells. Examples of these incidents are traumatic cerebrovascular disorder, traumatic neuropathic Alzheimer disease, AIDS encephalopathy, hepatic encephalopathy, anticancer drug-induced peripheral neuropathy and diabetic neuropathy. Drugs effective for these diseases are also desired.

It is extremely difficult to repair functions, or reconstruct cerebral higher functions, which have been lost by degeneration or death of nerve cells. Thus, how to prevent degeneration or death of nerve cells is of vital importance.

There are a class of synthetic compounds called growth hormone releasing peptide(GHRP)-like compounds or growth hormone secretagogues (GH secretagogues, GHS) (Bowers C. Y. (Cell. Mol. Life Sci.(1998) 54: 1316–1329), Smith R. G. et al. (Endocr. Rev.(1997) 18: 621–645)) which secrete growth hormone (GH). The mechanism of GH secretion is unknown, but is considered to be mediated by GHRP/GHS receptors present in the hypothalamus or the pituitary. GHRP/GHS receptors also exist in the cerebral cortex or the hippocampus (Mol. Brain Res.(1997) 48: 23–29, Endocrinology (1997)138: 4552–4557). The existence of GHRP/GHS receptors of a different subclass is also reported (Circ. Res.(1999) 85: 796–802). However, little has been known about the roles in the brain of growth hormone releasing peptide-like compounds or GH secretagogues mediated by these receptors.

DISCLOSURE OF THE INVENTION

The inventors of the present invention conducted in-depth studies in an attempt to discover a neuroprotective drug for preventing and treating diseases involving degeneration or death of nerve cells. As a result, they have found that a preparation containing a growth hormone secretion promoting substance as an active ingredient (hereinafter referred to as "the present preparation") is effective as a neuroprotective drug. Based on this finding, they have accomplished this invention.

BEST MODE FOR CARRYING OUT THE INVENTION

Figure 1:
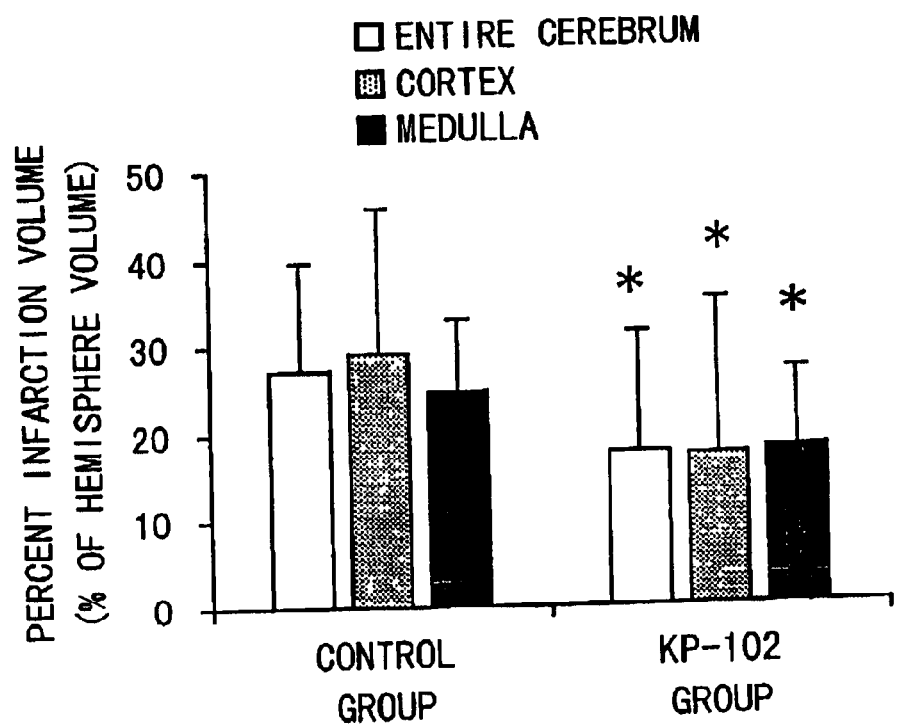
FIG. 1 is a view showing the effect of KP-102 on reduction of a cerebral infarction size in cerebral ischemia-reperfusion models.

According to an aspect of the present invention, there is provided an agent for prevention or treatment of diseases involving degeneration or death of nerve cells, characterized by containing a growth hormone secretion promoting substance as an active ingredient.

According to another aspect of the present invention, there is provided the agent for prevention or treatment of diseases involving ischemic degeneration or death of nerve cells, containing a growth hormone secretion promoting substance as an active ingredient.

According to still another aspect of the present invention, there is provided the agent for prevention or treatment of cerebrovascular disorders, containing a growth hormone secretion promoting substance as an active ingredient.

According to a further aspect of the present invention, there is provided the agent for prevention or treatment of cerebral infarction, containing a growth hormone secretion promoting substance as an active ingredient.

According to a still further aspect of the present invention, there is provided the agent for prevention or treatment of cerebral edema, containing a growth hormone secretion promoting substance as an active ingredient.

According to an additional aspect of the present invention, there is provided an agent for prevention or treatment of diseases involving degeneration or death of nerve cells, characterized by containing a substance acting on a growth hormone secretion promoting substance receptor as an active ingredient.

According to a still additional aspect of the present invention, there is provided a method for prevention or treatment of diseases involving degeneration or death of nerve cells, characterized by administering a pharmacologically effective amount of a growth hormone secretion promoting substance to a mammal including humans.

Herein, the "diseases involving degeneration or death of nerve cells" refer to diseases in which nerve cells underwent degeneration or death for some cause, for example, brain and nerve disorders including spinal cord disorder and peripheral nerve disorder. These diseases are roughly classified into those caused by ischemia (hereinafter referred to as "ischemic"), and those which are not ascribed to ischemia, but are due to various causes, such as trauma, infection, inflammation, tumor, metabolic disorder, degeneration, and drug intoxication (hereinafter referred to as "non-ischemic"). The "nerve cells" refer to cells constituting central nerves and peripheral nerves. The "brain and nerves" in the "brain and nerve disorders" refer to nerves of the brain comprising the cerebral hemispheres, cerebellum and brain stem, spinal nerves, and peripheral nerves. Therefore, the "brain and nerve disorders" referred to here have a wide meaning, rather than a narrow meaning (cranial nerve injury).

"Cerebral ischemia" refers to a diseased state in which a blood clot (thrombus), other factor obstructing the artery (embolus) or arteriosclerosis interrupts or decreases the bloodstream in the artery leading into the brain, causing brain dysfunction, and resulting in headache, dizziness, disturbed consciousness and syncope. With cerebral ischemia, a loss in the blood flow to a specific blood vessel area is known as focal cerebral ischemia, and a loss in the blood flow to the entire brain is known as global cerebral ischemia. Both types of ischemia also occur in hypotension or hypoxemia.

"Cerebrovascular disorders" refer to states in which ischemia or hemorrhage occurs owing to an abnormality in the cerebral blood vessel to affect the brain functionally or organically, and further refer to sequelae to these states. These disorders include cerebral hemorrhage and cerebral infarction.

"Cerebral infarction" refers to a state in which a brain tissue is necrotized by disturbance of the bloodstream in the cerebral blood vessel. Main causes of the disturbed bloodstream are cerebral thrombosis and cerebral embolism.

"Cerebral edema" refers to an excessive accumulation of fluid in the brain parenchyma, causing an increase in the brain volume.

Examples of neurological diseases involving degeneration or death of ischemic nerve cells are cerebrovascular disorders; migraine, and cerebrovascular ischemia caused by cocaine abuse; cerebral edema and hypernatremic cerebral disorder; cerebral ischemia including epilepsy or epileptic psychiatric symptoms; cerebral ischemia during surgical operation (ischemic tissue injury); cerebrovascular ischemia caused by head injury; and neonatal asphyxia.

The above-mentioned cerebrovascular disorders include cerebral infarction (e.g., cerebral thrombosis, cerebral embolism, lacunar cerebral infarction, asymptomatic cerebral infarction), and transient ischemic attack (TIA); reversible ischemic neurological deficit (RIND); vasospasm due to intracerebral hemorrhage or subarachnoid hemorrhage; cerebrovascular dementia; and cerebrovascular ischemia caused by cocaine abuse.

Examples of neurological diseases involving degeneration or death of non-ischemic nerve cells are, but not limited to, Alzheimer disease, vascular dementia, Pick disease, spino-cerebellar degeneration, chorea, AIDS encephalopathy, hepatic encephalopathy, Parkinson disease, amyotrophic lateral sclerosis, anticancer drug-induced peripheral neuropathy, diabetic neuropathy, traumatic neurological disorder, and secondary complications of these diseases.

As the "growth hormone secretion promoting substance receptors", several types of receptors are currently known. Typically, they are the aforementioned growth hormone releasing peptide (GHRP)/growth hormone secretagogue (GHS) receptors, which are a family of receptors including receptors called Type 1a and Type 1b discovered in experiments on binding to MK-0677 (Hormon Res., 1999, 51(suppl 3), 1, Science, 1996, 273, 974), receptors called FM1, FM2 and FM3 (Hormon Res., 1999, 51(suppl 3), 1, Endocrine Reviews, 1997, 18(5), 621), and receptors called a hexarelin binding site (Hormon Res., 1999, 51(suppl 3), 1, Endocrinology 1998, 139, 432, J. Clin. Endocrinol. Metab., 2000, 85, 3803). However, these publicly known receptors are not restrictive.

The "substances acting on the growth hormone secretion promoting substance receptors" refer to substances which act on (for example, bind to) any of the above-described receptors to activate the receptors. These substances include the growth hormone secretion promoting substances cited below.

The "growth hormone secretion promoting substances" according to the present invention include growth hormone releasing peptides (GHRP) and growth hormone secretagogues (GHS).

The "growth hormone releasing peptides (GHRP)" refer to peptides having the pharmacological activity that promotes growth hormone release. Various derivatives (for example, derivatives formed by substitution of amino acids constituting the peptides, ester derivatives) are also included, as long as these derivatives have functions equivalent to such function. There are no restrictions on the numbers and origins of the amino acid residues or amino acid derivative residues in the peptides (for example, the peptides or derivatives isolated or purified from human cells, synthetic products, semi-synthetic products, and those obtained by genetic engineering).

The "amino acid derivatives" include, for example, alkyl-substituted tryptophan, β-naphthylalanine, α-naphthylalanine, 3,4-dihydrophenylalanine, and methylvaline. The amino acids and amino acid derivatives include both of L forms and D-forms.

The "GH secretagogues" refer to non-peptide substances having the pharmacological activity that promotes growth hormone secretion. Various derivatives (for example, ester derivatives) are also included, as long as these derivatives have functions equivalent to such function.

Details of the "growth hormone secretion promoting substance" according to the present invention are disclosed, for example, in the following patent specifications. Furthermore, all of those classified in the following documents as growth hormone releasing peptides (GHRP), growth hormone releasing peptide(GHRP)-like compounds, growth hormone releasing peptide-mimetics (GHRP-mimetics), and growth hormone secretagogues (GH secretagogoes, GHS) are included in the growth hormone secretion promoting substances of the invention. However, such classifications are not strict, and are not to be interpreted as restrictive. WO00/48623, WO99/09991, WO99/08699, WO98/58950, WO98/58949, WO98/58948, WO98/58947, WO98/51687, WO98/50036, WO98/46569, WO98/46220, WO98/25897, WO98/25622, WO98/16527, WO98/10653, WO98/03473, WO97/42223, WO97/40071, WO97/40023, WO97/39768, WO97/34604, WO97/27298, WO97/25057, WO97/24369, WO97/23508, WO97/22622, WO97/22620, WO97/22367, WO97/21730, WO97/18233, WO97/15574, WO97/15573, WO97/15191, WO97/11697, WO97/00894, WO96/38471, WO96/35713, WO96/33189, WO96/32943, WO96/32126, WO96/24587, WO96/24580, WO96/22997, WO96/22782, WO96/15148, WO96/13265, WO96/10040, WO96/05195, WO96/02530, WO95/34311, WO95/17423, WO95/17422, WO95/16707, WO95/16692, WO95/16675, WO95/14666, WO95/13069, WO95/12598, WO95/09633, WO95/03290, WO95/03289, WO94/19367, WO94/18169, WO94/13696, WO94/11397, WO94/11012, WO94/08583, WO94/07519, WO94/07486, WO94/07483, WO94/05634, WO93/04081, WO92/16524, WO92/01711, WO89/10933, WO89/07111, WO89/07110, WO83/02272, U.S. Pat. No. 5,936,089, U.S. Pat. No. 5,877,182, U.S. Pat. No. 5,872,100, U.S. Pat. No. 5,854,211, U.S. Pat. No. 5,830,433, U.S. Pat. No. 5,817,654, U.S. Pat. No. 5,807,985, U.S. Pat. No. 5,804,578, U.S. Pat. No. 5,798,337, U.S. Pat. No. 5,783,582, U.S. Pat. No. 5,777,112, U.S. Pat. No. 5,776,901, U.S. Pat. No. 5,773,448, U.S. Pat. No. 5,773,441, U.S. Pat. No. 5,767,124, U.S. Pat. No. 5,767,118, U.S. Pat. No. 5,767,085, U.S. Pat. No. 5,731,317, U.S. Pat. No. 5,726,319, U.S. Pat. No. 5,726,307, U.S. Pat. No. 5,721,251, U.S. Pat. No. 5,721,250, U.S. Pat. No. 5,691,377, U.S. Pat. No. 5,672,596, U.S. Pat. No. 5,668,254, U.S. Pat. No. 5,663,171, U.S. Pat. No. 5,663,146, U.S. Pat. No. 5,656,606, U.S. Pat. No. 5,652,235, U.S. Pat. No. 5,646,301, U.S. Pat. No. 5,635,379, U.S. Pat. No. 5,583,130, U.S. Pat. No. 5,578,593, U.S. Pat. No. 5,576,301, U.S. Pat. No. 5,559,128, U.S. Pat. No. 5,545,735, U.S. Pat. No. 5,536,716, U.S. Pat. No. 5,534,494, U.S. Pat. No. 5,506,107, U.S. Pat. No. 5,494,919, U.S. Pat. No. 5,492,920, U.S. Pat. No. 5,492,916, U.S. Pat. No. 5,486,505, U.S. Pat. No. 5,434,261, U.S. Pat. No. 5,430,144, U.S. Pat. No. 5,416,073, U.S. Pat. No. 5,374,721, U.S. Pat. No. 5,317,017, U.S. Pat. No. 5,310,737, U.S. Pat. No. 5,284,841, U.S. Pat. No. 5,283,241, U.S. Pat. No. 5,206,235, U.S. Pat. No. 5,030,630, U.S. Pat. No. 4,880,777, U.S. Pat. No. 4,851,408, U.S. Pat. No. 4,650,787, U.S. Pat. No. 4,485,101, U.S. Pat. No. 4,411,890, U.S. Pat. No. 4,410,513, U.S. Pat. No. 4,410,512, U.S. Pat. No. 4,228,158, U.S. Pat. No. 4,228,157, U.S. Pat. No. 4,228,156, U.S. Pat. No. 4,228,155, U.S. Pat. No. 4,226,857, U.S. Pat. No. 4,224,316, U.S. Pat. No. 4,223,021, U.S. Pat. No. 4,223,020, and U.S. Pat. No. 4,223,019.

(The contents of these documents are included herein for reference).

Concrete compounds as growth hormone releasing peptides (GHRP) are exemplified by, but not limited to, pralmorelin, hexarelin, GHRP-1, GHRP-6 (SK&F-110679), ghrelin and ghrelin analogues, ipamorelin (NNC-260161), NNC-260194 and NNC-260235, and salts and esters thereof.

Examples of these salts are described below, and hydrochlorides are named as preferred examples (e.g., pralmorelin dihydrochloride, hexarelin hydrochloride).

Ghrelin is a peptide having 28 amino acids which is shown by the chemical structure described in a table to be offered later. Ghrelin analogues include those in which one or more of the 28 amino acids have been deficient or substituted, or those to which one or more amino acids have been added, as long as they have a growth hormone secretion promoting action. Furthermore, various derivatives of them are included [for example, derivatives with peptide-constituting amino acids substituted (those having a group, such as an alkylene group, inserted between the amino acids are also included) and ester derivatives].

No restrictions are imposed on the origins of the amino acid residues or amino acid derivative residues in the peptides (for example, the peptides or derivatives may have been isolated or purified from human or rat cells, or may be synthetic products or semi-synthetic products, or may have been obtained by genetic engineering).

Examples of the peptide in which one or more of the 28 amino acids have been deficient or substituted, or the peptide to which one or more amino acids have been added are mentioned below.

Examples of ghrelin in which one of the amino acids has been deficient are typified by des-Gln14-ghrelin, i.e., ghrelin with the 14th Gln residue deleted.

The ghrelin analogues of the present invention also include the following compounds described in J. Med. Chem. 2000, 43, 4370–4376.

Examples are peptides and their derivatives which have the third and fourth amino acids from the N-terminal among the 28 amino acids of ghrelin (preferably, the four amino acids at the N-terminal) and in which the side chain of the third amino acid (Ser) from the N-terminal has been substituted, the peptides and derivatives having a growth hormone secretion promoting action.

Examples of the side chain of the third amino acid from the N-terminal are an acyl group and an alkyl group (the number of their carbon atoms is preferably 6 to 18) other than octanoyl which is the side chain of ghrelin.

Concrete examples of the side chain are as follows: —$CH_2(CH_2)_9CH_3$, —$CO$—$(CH_2)_6CH_3$, —$CO$—$CH=CH$—$CH=CH$—$CH=CH$—$CH_3$, —$CO$—$CH(CH_2CH_2CH_3)_2$, —$CO$—$(CH_2)_9CH_3$, —$CO$—$(CH_2)_{14}CH_3$, —$CO$—$(CH_2)_6CH_2Br$, —$CO$—$CH(CH_2)_2CONH(CH_2)_2CH_3$, —$COPh$, and a group of the following formula

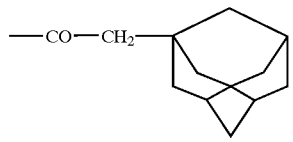

A concrete example of the ghrelin analogue, which has the third and fourth amino acids from the N-terminal and in which the side chain of the third amino acid (Ser) from the N-terminal has been substituted, is the compound reported at the 37th Peptide Forum (Oct. 18 to 20, 2000), i.e., $NH_2$—$(CH_2)_4$—CO-Ser(octyl)-Phe-Leu-NH—$(CH_2)_2$—$NH_2$

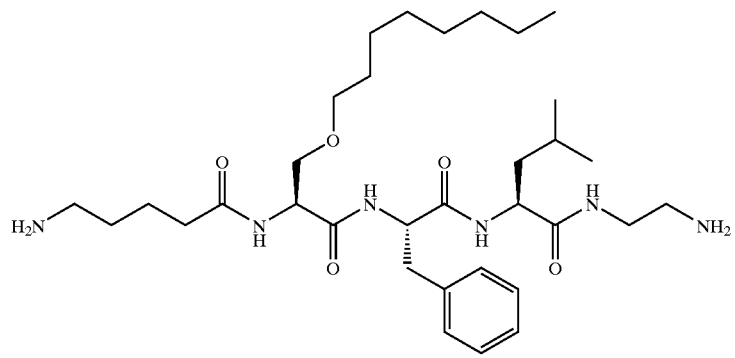

The GH secretagogues (GHS) include compounds expressed by the following formulae:

(1) Compounds of the following general formula

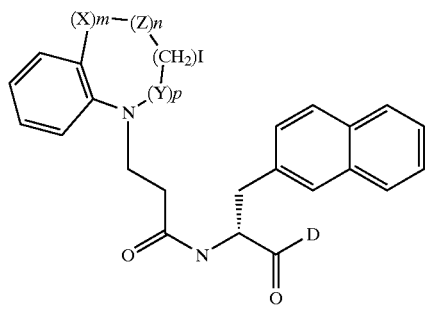

where
l denotes 0, 1 or 2,
X represents —$CH_2$—, —O—, —S(O)r- (r=0, 1 or 2), —C(O)—, —C(S)—, —CH=CH—, —CH(OH)— or —NR—, R represents a hydrogen atom, a ($C_1$–$C_5$) alkyl group, a ($C_3$–$C_8$)cycloalkyl group, an acyl group or an alkoxycarbonyl group, m denotes 0, 1 or 2, Y represents —C(O)—, —C(S)—, or a ($C_1$–$C_5$)alkylene group which may be substituted by ($C_1$–$C_5$)alkyl group(s), p denotes 0, 1 or 2, Z represents a substituted or unsubstituted ($C_1$–$C_5$) alkylene group, —NR— (R is a hydrogen atom, a ($C_1$–$C_5$)alkyl group, a ($C_3$–$C_8$)cycloalkyl group, an acyl group or an alkoxycarbonyl group), or a group of the formula

where A is a 5- or 6-membered aromatic ring optionally containing at least one hetero atom, and A may further be substituted by a group selected from a halogen atom, a hydroxyl group, a ($C_1$–$C_5$)alkyl group, a ($C_1$–$C_5$)alkoxy group, a ($C_1$–$C_5$)perfluoroalkyl group, a ($C_1$–$C_5$)perfluoroalkoxy group, a nitro group, a cyano group, an amino group, a substituted amino group, a phenyl group and/or a substituted phenyl group, n denotes 0 or 1, D represents

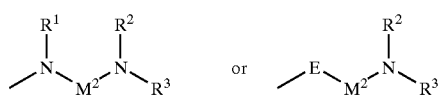

where $R^1$ represents a hydrogen atom, an alkyl group, a substituted alkyl group, a cycloalkyl group or a substituted cycloalkyl group, $R^2$ and $R^3$ each represent, independently of each other, a hydrogen atom, an alkyl group, a substituted alkyl group, an acyl group, an amidino group or an alkoxycarbonyl group, or one of $R^2$ and $R^3$, taken together with $R^1$, may constitute an alkylene group, further, $R^2$ and $R^3$ may together constitute an alkylene group or a hetero ring, $M^2$ is represented by the formula $$—(CH_2)x—\underset{R^6}{\overset{R^5}{\underset{|}{\overset{|}{C}}}}—(CH_2)y—\underset{R^8}{\overset{R^7}{\underset{|}{\overset{|}{C}}}}—(CH_2)z—$$

$$—(CH_2)x—\overset{R^5}{\underset{|}{C}}=\overset{R^7}{\underset{|}{C}}—(CH_2)z— \quad \text{or}$$

$$—(CH_2)x—C\equiv C—(CH_2)z—$$

where x, y and z each represent, independently of each other, an integer of 0 to 4, $R^5$, $R^6$, $R^7$ and $R^8$ each represent, independently of each other, a hydrogen atom, a halogen atom, an alkyl group, a substituted alkyl group, —$OR^9$, —$SR^9$, —$NR^9R^{10}$, —$NHC(O)R^9$, —$C(O)OR^9$, —$OCOR^9$, —$OC(O)OR^9$ or —$CONR^9R^{10}$, or may constitute an alkylene group or a hetero ring taken together with $R^1$ or $R^2$, $R^9$ and $R^{10}$ each represent, independently of each other, a hydrogen atom, an alkyl group or a substituted alkyl group, $R^9$ may constitute an alkylene group taken together with $R^1$ or $R^2$, $R^5$ and $R^7$, or $R^6$ and $R^8$ may together constitute an alkylene group or a hetero ring, or $R^5$ and $R^6$, or $R^7$ and $R^8$ may constitute a carbonyl group, a thiocarbonyl group or an imino group taken together with the carbon atom to which $R^5$ and $R^6$, or $R^7$ and $R^8$ have been bound, and E represents an oxygen atom or a sulfur atom.

Of the compounds (1), preferred compounds are those of the above-mentioned formula where l denotes 0, 1 or 2, preferably 0, X represents —$CH_2$—, —O—, —$S(O)r$-, —$C(O)$—, —$C(S)$—, —$CH=CH$—, —$CH(OH)$— or —NR—, R represents a hydrogen atom, a ($C_1$–$C_5$) alkyl group, a ($C_3$–$C_8$)cycloalkyl group, an acyl group, or an alkoxycarbonyl group, r denotes 0, 1 or 2, m denotes 0, 1 or 2, preferred being —$CH_2$— as X and m as 2, Y represents —$C(O)$—, —$C(S)$—, or a ($C_1$–$C_5$)alkylene group which may be substituted by ($C_1$–$C_5$)alkyl group(s), p denotes 0, 1 or 2, preferred being —$C(O)$— as Y, and 1 as p, Z represents a substituted or unsubstituted ($C_1$–$C_5$) alkylene group, —NR— (R is a hydrogen atom, a ($C_1$–$C_5$)alkyl group, a ($C_3$–$C_8$)cycloalkyl group, an acyl group or an alkoxycarbonyl group), or a 6-membered aromatic ring represented by the formula n denotes 0 or 1, and D represents a group of the formula $$\underset{H}{N}\diagdown\overset{OH}{\underset{*}{\diagup\diagdown}}NH_2$$

In the above formula, the asterisk (*) represents an asymmetric center, so that isolated pure optical isomers, partially purified optical isomers or racemic mixtures are included.

(2) Compounds of the following general formula where $R^A$ represents a substituted or unsubstituted alkyl, a substituted or unsubstituted cycloalkyl, a substituted or unsubstituted alkoxy, a substituted or unsubstituted aryl, or a substituted or unsubstituted amino, X represents a single bond, —CO— or —$SO_2$—, D represents $$\underset{M^2}{\overset{R^1}{\underset{|}{N}}}\diagdown\overset{R^2}{\underset{|}{N}}\diagdown R^3 \quad \text{or} \quad \underset{M^2}{\overset{E}{\diagdown}}\overset{R^2}{\underset{|}{N}}\diagdown R^3$$

where $R^1$ represents a hydrogen atom, an alkyl group, a substituted alkyl group, a cycloalkyl group, or a substituted cycloalkyl group, $R^2$ and $R^3$ each represent, independently of each other, a hydrogen atom, an alkyl group, a substituted alkyl group, an acyl group, an amidino group or an alkoxycarbonyl group, or either $R^2$ or $R^3$ and $R^1$ may together constitute an alkylene group, further, $R^2$ and $R^3$ may together constitute an alkylene group or a hetero ring, $M^2$ is represented by the formula $$—(CH_2)x—\underset{R^6}{\overset{R^5}{\underset{|}{\overset{|}{C}}}}—(CH_2)y—\underset{R^8}{\overset{R^7}{\underset{|}{\overset{|}{C}}}}—(CH_2)z—$$

$$—(CH_2)x—\overset{R^5}{\underset{|}{C}}=\overset{R^7}{\underset{|}{C}}—(CH_2)z— \quad \text{or}$$

$$—(CH_2)x—C\equiv C—(CH_2)z—$$

where x, y and z each represent, independently of each other, an integer of 0 to 4, $R^5$, $R^6$, $R^7$ and $R^8$ each represent, independently of each other, a hydrogen atom, a halogen atom, an alkyl group, a substituted alkyl group, —$OR^9$, —$SR^9$, —$NR^9R^{10}$, —$NHC(O)R^9$, —$C(O)OR^9$, —$OCOR^9$, —$OC(O)OR^9$ or —CONR$^9$R$^{10}$, or may constitute an alkylene group or a hetero ring taken together with R$^1$ or R$^2$, R$^9$ and R$^{10}$ each represent, independently of each other, a hydrogen atom, an alkyl group or a substituted alkyl group, R$^9$ may constitute an alkylene group taken together with R$^1$ or R$^2$, R$^5$ and R$^7$, or R$^6$ and R$^8$ may together constitute an alkylene group or a hetero ring, or R$^5$ and R$^6$, or R$^7$ and R$^8$ may constitute a carbonyl group, a thiocarbonyl group or an imino group taken together with the carbon atom to which R$^5$ and R$^6$, or R$^7$ and R$^8$ have been bound, and E represents an oxygen atom or a sulfur atom, and the asterisk (*) represents an asymmetric center, so that the compounds (2) include isolated pure optical isomers, partially purified optical isomers, racemic mixtures or diastereomer mixtures (all such optical isomers are included in the scope of the present invention).

Of the compounds (2), preferred aspects are as follows:

X is preferably —CO—.

R$^A$ is preferably a C$_1$–C$_{11}$ alkyl which may be substituted by a substituted or unsubstituted cycloalkyl, a substituted or unsubstituted alkoxy, a substituted or unsubstituted aryl and/or a hydroxy; a C$_3$–C$_6$ cycloalkyl which may be substituted by a substituted or unsubstituted alkyl, a substituted or unsubstituted alkoxy, a substituted or unsubstituted aryl and/or a hydroxy; a C$_1$–C$_{11}$ alkoxy which may be substituted by a substituted or unsubstituted cycloalkyl, a substituted or unsubstituted alkoxy, a substituted or unsubstituted aryl and/or a hydroxy; an aryl which may be substituted by a substituted or unsubstituted cycloalkyl, a substituted or unsubstituted alkoxy, a substituted or unsubstituted aryl and/or a hydroxy; or an amino which may be substituted by a substituted or unsubstituted alkyl or a substituted or unsubstituted aryl.

More preferably, R$^A$ is represented by any of the following formulas:

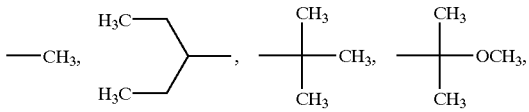

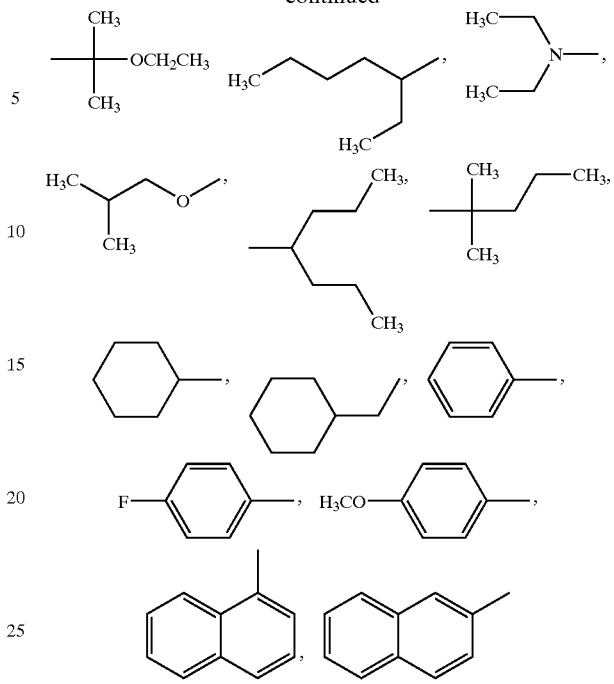

D is preferably represented by the following formula:

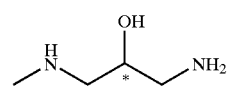

Concrete compounds as the GH secretagogues (GHS) are exemplified by, but not restricted to, S-38855, S-37555, S-39100, ibutamorelin [e.g., ibutamorelin mesylate (MK-0677)], capromorelin (CP-424391), NNC-260722, NNC-260323, L-163661, L-163540, L-168721, LY-426410, LY-444711, L-692,429, L-692,585, L-700,653, L-252,564, L-162,752, L-164,080, G-7203, G-7039, G-7052, G-7220, tabimorelin (NN-703), or salts and esters thereof. These exemplary salts are tabulated below, and hydrochlorides are named as preferred examples.

Typical of the above-described compounds are described in detail in the following table:

Chemical Names and Structural Formulas of Compounds as Concrete Examples

| General Name | Chemical Name | Chemical Structure |
|---|---|---|
| Pralmorelin (GHRP-2) | D-alanyl-3-(2-naphthalenyl)-D-alanyl-L-alanyl-L-tryptophyl-D-phenylalanyl-L-lysineamide | H-D-Ala-D-2-Nal-Ala-Trp-D-Phe-Lys-NH$_2$ |
| Hexarelin (examorelin) | L-histidyl-2-methyl-D-tryptophyl-L-alanyl-L-tryptophyl-D-phenylalanyl-L-lysineamide | H-His-D-2-Me-Trp-Ala-Trp-D-Phe-Lys-NH$_2$ |
| GHPR-6 (SK&F-110679) | L-histidyl-D-tryptophyl-L-alanyl-L-tryptophyl-D-phenylalanyl-L-lysineamide | H-His-D-Trp-Ala-Trp-D-Phe-Lys-NH$_2$ |
| GHRP-1 | | Ala-His-D-(2')-Nal-Ala-Trp-D-Phe-Lys-NH$_2$ |
| Ghrelin | | GSSFLSPEHQKAQQRKESKKPPAKLQPR<br>        \|<br>        O<br>        \|<br>(C=O)—(CH$_2$)$_6$—CH$_3$<br>Rat type<br>KA (underlined) ⇒ RV (human type) |

-continued

Chemical Names and Structural Formulas of Compounds as Concrete Examples

| General Name | Chemical Name | Chemical Structure |
| --- | --- | --- |
| S-38855 | N-(3-amino-2-hydroxypropyl)-2(R)-[1-(2,2-dimethylpropionyl)pyrrolidine-2(S)-carbonylamino]-3-naphthalen-2-yl-propionamide | 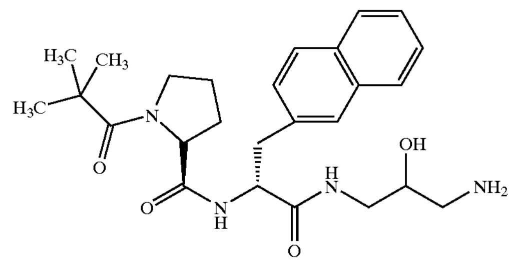 |
| S-37555 | N-[1(R)-(3-amino-2-hydroxy-propylcarbamoyl)-2-yl-ethyl]-3-(6-oxo-11,12-dihydro-6H-dibenzo[b,f]azocinn-5-yl)-propionamide | 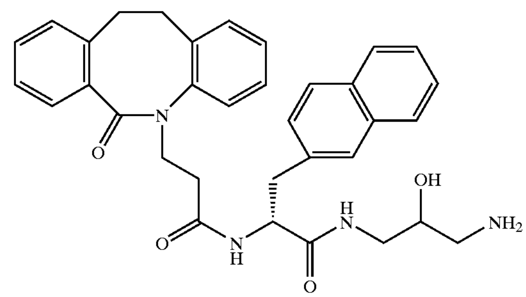 |
| S-39100 | N-(3-amino-2-hydroxypropyl)-2(S)-[1-(2-ethylbutyryl)pyrrolidine-2(R)-carbonylamino]-3-naphthalen-2-yl-propionamide | 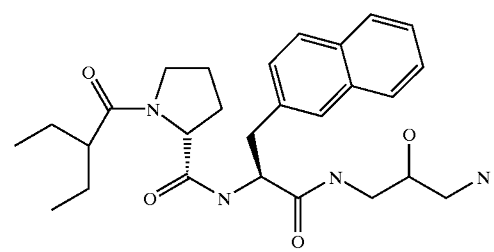 |
| MK-0677 (ibutamorelin mesylate) | 2-Amino-N-[(R)-2-(benzyloxy)-1-[[1-(methylsulfonyl)spiro[indoline-3,4'-piperidin]-1'-yl]carbonyl]ethyl]-2-methylpropionamidomonomethanesulfonate | 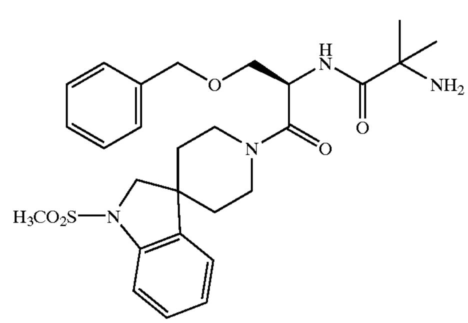 |
| CP-424391 (Capromorelin) | 2-Amino-N-[(1R)-1-[[(3aR)-3a-benzyl-2,3,3a,4,6,7-hexahydro-2-methyl-3-oxo-5H-pyrazolo[4,3,c]pyridin-5-yl]carbonyl]-2-(benzyloxy)ethyl]-2-methylpropionamide | 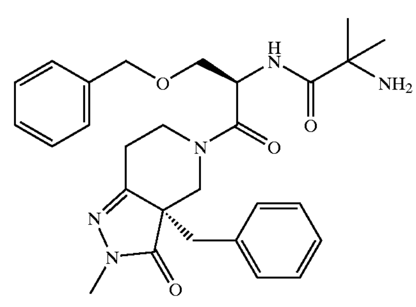 |

-continued

Chemical Names and Structural Formulas of Compounds as Concrete Examples

| General Name | Chemical Name | Chemical Structure |
| --- | --- | --- |
| NNC-260703 (Tabimorelin) NN-703 | 5-Amino-5-methylhexa-(2E)-enoic acid N-methyl-N-[(1R)-1-[N-methyl-N-[(1R)-1-(methylcarbamoyl)-2-phenylethyl]carbamoyl]-2-(2-naphthyl)ethyl]amide | 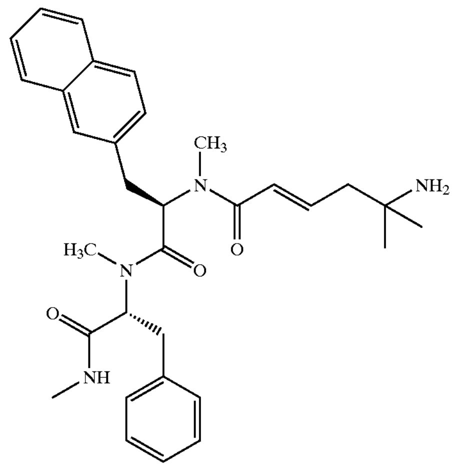 |
| NNC-260722 | 5-Amino-5-methylhexa-(2E)-enoic acid N-methyl-N-[(1R)-1-[N-methyl-N-[(1R)-1-(2-hydroxypropylcarbamoyl)-2-phenylethyl]carbamoyl]-2-(2-naphthyl)ethyl]amide | 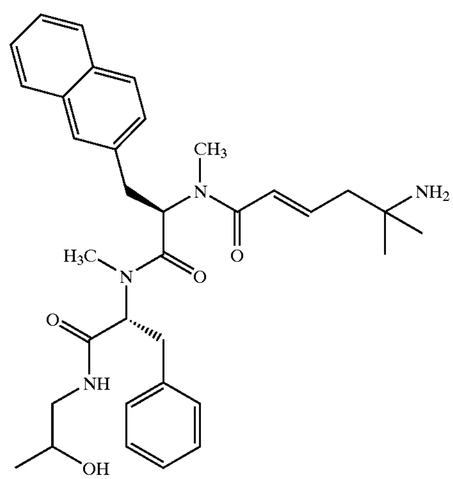 |
| NNC-260194 | 3-(4-Imidazolyl)propionyl-D-Phe-Ala-Trp-D-Phe(CH$_2$NH)-Lys-NH-ol | |
| NNC-260235 | 3-Aminomethyl-benzoyl-D-2-Nal-N-Me-D-Phe-Lys-NH$_2$ | 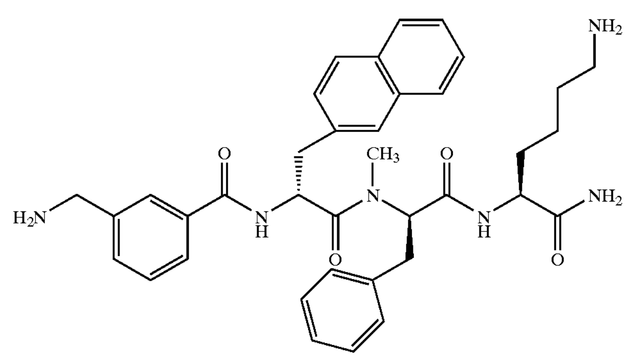 |

-continued

Chemical Names and Structural Formulas of Compounds as Concrete Examples

| General Name | Chemical Name | Chemical Structure |
| --- | --- | --- |
| NNC-260323 | (2R)-2-[N-(3-aminomethylbenzoyl)-N-methyl-D-2-Nal]-N-methyl-3-phenyl-1-propanol | 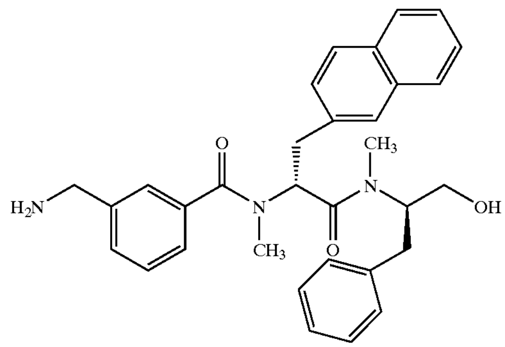 |
| NNC-260161 (ipamorelin) | 2-Methylalanyl-L-histidyl-3-(2-naphthalenyl)-D-alanyl-D-phenylalanyl-L-lysineamide | 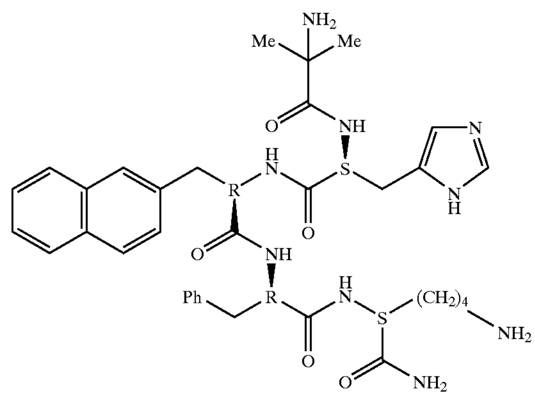 |
| L-163540 | 1-[2(R)-(2-amino-2-methylpropionylamino)-3-(1H-indol-3-yl)propionyl]3-benzylpiperidine-3(S)-carboxylic acid ethyl ester | 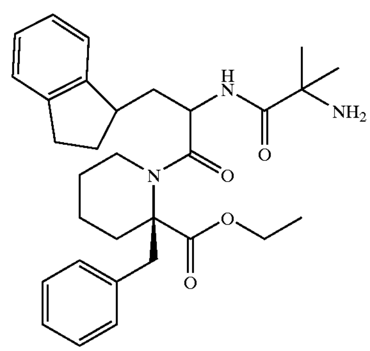 |
| L-168721 | N-(6-aminohexyl)-2-(4-oxo-2-phenethyl-6-phenyl-4H-quinazolin-3-yl)acetamide | 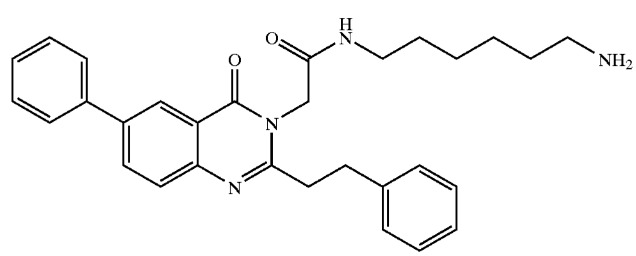 |

-continued

Chemical Names and Structural Formulas of Compounds as Concrete Examples

| General Name | Chemical Name | Chemical Structure |
| --- | --- | --- |
| LY-426410 | 2-Amino-N-[2-benzyloxy-(1R)-[1-[(1R)-(4-methoxyphenyl)-2-(4-methylpiperidin-1-yl)-2-oxo-ethyl]-1H-imidazol-4-ylcarbamoyl]ethyl]-2-methylpropionamide | 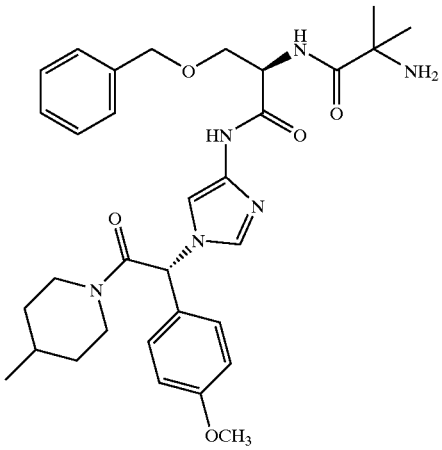 |
| LY-444711 | 2-Methylalanyl-N-[1-[(1R)-1-(4-methoxyphenyl)-1-methyl-2-oxo-2-(1-pyrrolidinyl)ethyl]-1H-imidazol-4-yl]-5-phenyl-D-norvalineamide | 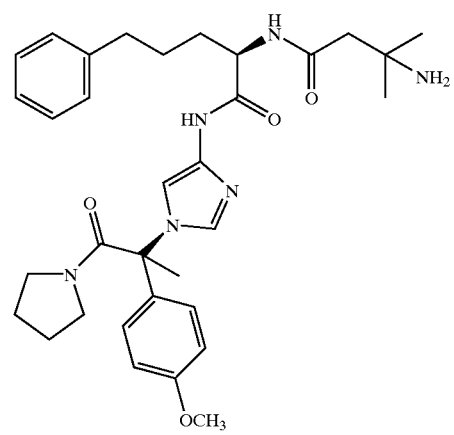 |

Salts of the above-described compounds include, for example, salts with mineral acids such as hydrochloric acid, sulfuric acid or phosphoric acid, salts with organic acids such as methanesulfonic acid, benzenesulfonic acid, malic acid, citric acid or succinic acid, salts with alkali metals such as sodium or potassium, salts with alkaline earth metals such as calcium or magnesium, and salts with basic amino acids such as arginine.

In the preparation of the present invention, the growth hormone secretion promoting substances and their salts may be used in combination of two or more.

The growth hormone secretion promoting substance used in the present invention can be formed into ordinary oral preparations and parenteral preparations, for example, liquids and solutions (injections, nasal drops, syrups, dry syrups), tablets, troches, capsules (hard capsules, soft capsules, microcapsules), powder, subtle granules, granules, ointments and suppositories, by publicly known pharmaceutical manufacturing techniques, when used alone or combined with pharmaceutically acceptable carriers, additives, etc. The growth hormone secretion promoting substance of the invention can also be made into dosage forms, such as drug delivery systems (for example, slow-release preparations).

The carriers and additives usable in the preventive/therapeutic agents of the present invention include, for example, those which are ordinarily used in preparing pharmaceuticals: aqueous vehicles such as physiological saline, water (tap water, distilled water, purified water, water for injection) and Ringer solution, nonaqueous vehicles such as oily solvents (vegetable oils) and water-soluble solvents (propylene glycol, macrogol, ethanol, glycerin), bases such as cacao butter, polyethylene glycol, microcrystalline wax, white beeswax, liquid petrolatum and white petrolatum, excipients such as sucrose, starch, mannitol, sorbitol, lactose, glucose, cellulose, talc, calcium phosphate and calcium carbonate, binders such as cellulose, methylcellulose, hydroxypropylcellulose, polypropylpyrrolidone, gelatin, acacia, polyethylene glycol, sucrose and starch, disintegrators such as starch, carboxymethylcellulose, hydroxypropyl starch, sodium bicarbonate, calcium phosphate, calcium carboxymethylcellulose and calcium citrate, lubricants such as magnesium stearate, talc and sodium lauryl sulfate, taste correctives such as citric acid, menthol, glycine, sorbitol and orange powder, preservatives and antiseptics such as parahydroxybenzoate esters, benzyl alcohol, chlorobutanol and quaternary ammonium salts (benzalkonium chloride, benzethonium chloride), stabilizers such as albumin, gelatin, sorbitol and mannitol, suspending agents such as methylcellulose, polyvinylpyrrolidone and aluminum stearate, plasticizers such as glycerin and sorbitol, dispersing agents such as hydroxypropyl methylcellulose, solution adjuvants such as hydrochloric acid and cyclodextrin, emulsifying agents such as sodium monostearate, electrolytes such as sodium chloride, and nonelectrolyte tonicity regulating agents and flavors, such as sugar alcohols, sugars and alcohols.

In the oral preparation, water-swellable cellulose (carboxymethylcellulose, calcium carboxymethylcellulose, sodium croscarboxymethylcellulose, low substitution degree hydroxypropylcellulose), such as microcrystalline cullulose ("Avicel" [trade name, a product of Asahi Chemical Industry]) as described in Japanese Unexamined Patent Publication No. 1998–456194 can be incorporated for increasing absorbability.

Normally, the preparation of the present invention is administered to mammals (e.g., mouse, rat, hamster, rabbit, cat, dog, cattle, horse, sheep, monkey), including humans, by the oral route or by such means as subcutaneous injection, nasal dropping, intraarterial injection (including drip infusion), intravenous injection, intraspinal injection or local cerebral administration.

The dose of the preparation of the invention differs according to the age, body weight or symptoms of the patient, and the route of administration. When used in treatment for adults (body weight 50 to 70 kg), the preparation of the invention, as a growth hormone secretion promoting substance, can be administered in a dose of about 20 $\mu$g to 20 mg per kg of body weight for oral administration, or about 0.1 to 1,000 $\mu$g per kg of body weight for intravenous administration, as a single daily dose regimen or as two to four divided portions per day.

The preventive/therapeutic agent of the present invention can be used simultaneously with, or at time intervals relative to, anti-dementia agents, nitrogen monoxide inhibitors, glutamate antagonists and blood vessel thickening inhibitors, in addition to cerebral circulation and blood flow improvers, platelet aggregation inhibitors, blood coagulation inhibitors, cerebral metabolic agents, antihypertensive agents, antidiabetic agents, anti-cerebral edema agents, thrombolytic agents, lipid metabolism improvers and free radical scavengers.

Concrete examples of the agents that can be used in combination with the preparation of the present invention are vinpocetine as an agent for improving cerebral circulation and blood flow, aspirin, ozagrel sodium and beraprost sodium as platelet aggregation inhibitors, heparin and argatroban as blood coagulation inhibitors, idebenone as a cerebral metabolic improver, delapril hydrochloride, manidipine hydrochloride and candesartan cilexetil as antihypertensive agents, voglibose and sulfonylurea derivatives as antidiabetic agents, glycerol as an anti-cerebral edema agent, tissue plasminogen activator and prourokinase as thrombolytic agents, pravastatin and clofibrate as lipid metabolism improvers, and vitamins E and C as free radical scavengers.

INDUSTRIAL APPLICABILITY

It was clarified for the first time by the present invention that the growth hormone secretion promoting substance is effective as a neuroprotective agent for preventing or treating diseases involving degeneration or death of nerve cells. The preventive/therapeutic agent containing the growth hormone secretion promoting substance of the present invention as an active ingredient has low toxicity against various animals, is highly safe in humans, and shows excellent effects of reducing the size of a cerebral infarct, diminishing cerebral edema, and alleviating neurologic symptoms. Furthermore, the preparation of the present invention directly affects nerve cells, and exhibits the action of suppressing degeneration or death of nerve cells. Thus, the preparation of the present invention is effective for prevention or treatment of diseases involving degeneration or death of nerve cells.

The present invention will now be described concretely by showing Preparation Examples and Test Examples, which in no way restrict the invention.

PREPARATION EXAMPLE 1

Pralmorelin dihydrochloride (hereinafter referred to as KP-102) was dissolved in physiological saline to prepare 0.1, 0.2 and 0.5 w/v % of solutions (injections). KP-102 was a synthetic product.

PREPARATION EXAMPLE 2

Empty gelatin capsules were charged with 11 mg of KP-102 and 189 mg of lactose to prepare capsules.

TEST EXAMPLE 1

Preventive and Therapeutic Effect of KP-102 in Rat Ischemia-Reperfusion Cerebral Infarction Models After Transient Obstruction of Middle Cerebral Artery The effect of the growth hormone secretion promoting substance was evaluated using ischemia-reperfusion cerebral infarction models, which are general pathological models of diseases involving degeneration or death of nerve cells, such as cerebral ischemia, cerebral infarction and cerebral edema. KP-102 was used as a typical example of the growth hormone secretion promoting substance.

1. Materials

KP-102 (synthetic product) was dissolved in physiological saline (JP) to a concentration of 24 $\mu$g/ml. Other reagents used were halothane (JP: Takeda Chem. Ind.), triphenyltetrazolium chloride (TTC, Nacalai tesque), Dulbecco PBS(−) (Nissui Pharmaceutical) and low viscosity dental impression silicone (XANTOPRENRL, imported by Hereus Dental Material, Osaka). A 1% TTC solution was prepared by dissolving TTC in an isotonic phosphate buffer solution (pH 7.4) which had been prepared by dissolving PBS(−) powder in distilled water.

Male Wistar rats (Charles River Japan, INC.), 9 weeks old and weighing about 300 g, were used as experimental animals.

2. Methods

1) Induction of Cerebral Infarct

Obstruction of the middle cerebral artery was performed in accordance with the method of Koizumi et al. (Jpn. J. Stroke (1986)8:1–8) and the method of Longa et al. (Stroke (1989)20:84–91). Anesthesia was performed with 2% halothane in a 30% oxygen/70% nitrous oxide mixed gas. A cannula for administration of a test material had been inserted into the right femoral vein, and the other end of the cannula delivered to the poll. After several hours or more, the animals were anesthetized again, and set in a supine position. A median incision of the neck was made, and connective tissues around the right common carotid artery, the internal carotid artery, and the external carotid artery were ablated. The distal end of the external carotid artery was ligated with a suture, and blood flow of the external carotid artery and the common carotid artery was blocked with a clip. The following procedure was performed, with measures for prevention of bleeding being taken: A small incision was made in the external carotid artery, and a plug comprising a 5 mm front end of a surgical 4-0 nylon thread coated with dental silicone was inserted toward the internal carotid artery as far as a site where a slight resistance was felt. As a result, the middle cerebral artery (hereinafter referred to as MCA) was occluded, at its point of origin, with the plug. The plug was fixed in the internal carotid artery with a clip. The incision wound was closed and anesthesia was stopped to awake the animals. Anesthesia was performed again 70 minutes after MCA occlusion, the plug was detached 75 minutes later to restore blood flow in MCA, and the end of the external carotid artery proximal to the incision site was closed for prevention of bleeding. Blood flow in the common carotid artery was restored 10 minutes later. The incision site of the skin was closed with a Michel needle, and the animals were recovered from anesthesia.

2) Administration of Test Material

The cannula for administration of the test material was connected to a free moving device (TCS2-21, Tsumura). Using an infusion pump (STC-531, Terumo or FP-W-100, Toyo Sangyo), KP-102 or a solvent (physiological saline, JP) for a control group was administered for 10 minutes at an infusion speed of 4 ml/kg/hr, beginning 30 minutes after MCA occlusion, and then administered continuously for 3 hours at an infusion speed of 2 ml/kg/hr. The total amount of KP-102 administered was 0.16 mg/kg. Upon completion of the treatment, the animal was released from the free moving device, and the end of the cannula was fused for closure. The cannula was retained in the body of the animal.

3) Measurement of Cerebral Infarct Size

Seventy-two hours after reperfusion, the animals were each ether-anesthetized, and bled to death by abdominal aortotomy. Immediately, decapitation was performed, and the brain was isolated. The brain was immersed in physiological saline cooled on ice, and the bottom of the brain was observed. After full cooling, an area ranging from the frontal pole to the occipital pole was cut at equal intervals (2 mm) using a brain mold slicer (RBM-40000, ASI Instruments, United States) to prepare eight coronary sections (designated as CS0, CS1, CS2, CS3, CS4, CS5, CS6 and CS7 in this sequence from the frontal side). Preparation of these sections was adjusted such that the optic chiasms fell on the surface of the fourth section. The CS1 to CS6 sections, as specimens, were each immersed in a 1% TTC solution, and incubated for 30 minutes at 37° C. for staining. Then, the rear surface was photographed to prepare slides.

The slide image was taken into an image analyzer (SP1000, OLYMPUS OPTICAL) to determine the proportion of the infarction site. Portions stained deep red with TTC were evaluated as normal regions, while white portions and less red portions (pink zones) than the normal hemisphere were evaluated as infarction regions. For the cortex, medulla and whole of the cerebrum, the infarction areas were calculated by the indirect method [the infarction area of the right cerebral hemisphere=the area of the left cerebral hemisphere−the normal area of the right cerebral hemisphere] based on the method of Lin T-N et al. (Stroke (1993)24:117–121). The volume ($mm^3$) of the brain was calculated by multiplying the area ($mm^2$) by the thickness (2 mm). The size of the brain differs from individual to individual. To make a correction for this individual variation, the percentage of the right cerebral hemisphere infarction volume to the left cerebral hemisphere volume was calculated as the percent infarction volume. The increase in the right cerebral volume due to edema (i.e., right hemisphere volume−left hemisphere volume) was expressed as a percentage to the left hemisphere volume, and taken as percent edema.

4) Other Measurement Parameters

At 75 minutes after initiation of ischemia and 1, 24 and 72 hours after reperfusion, the body temperature (rectal temperature) was measured with a body temperature controller (ATB-1100, NIHON KOHDEN) by inserting the front end of a measuring probe 5 cm deep from the anus.

At 1 hour after initiation of ischemia and 1, 24 and 72 hours after reperfusion, neurologic symptoms were observed, and expressed as scores by a unique evaluation method (Table 1) established based on the method of Longa et al. (Stroke(1989)20:84–91), the method of Garcia et al. (Stroke(1995)26:627–634), the method of Relton et al. (Stroke(1997)28:1430–1436), the method of Tupper et al. (Acta Neurobiol. Exp.(1980)40:999–1003), and Bederson et al. (Stroke(1986)17:472–476). The normal score was 33 points.

TABLE 1

Scale for Evaluation of Neurologic Symptoms

| Test | 0 | 1 | 2 | 3 | 4 | Ref. |
|---|---|---|---|---|---|---|
| Forelimb flexion while held in the air by tail | No movement on left side | Slight movement on left side | Slower movement on left side | Symmetrical movement | | 1 |
| Duration of forelimb flexion | >8 sec | >6 sec | >4 sec | >2 sec | ≦2 sec | 1 |
| Fourpaw outstreching while held by tail (walk on forelimbs) | No movement on left side | Left circling | Walking to the left | Symmetrical walking | | 1 |
| Symmetry in the movement of four limbs | Left circling | Walking to the left | Normal walking | | | 2 |
| Right forelimb placing test (leg hanging) | >8 sec | >6 sec | >4 sec | >2 sec | ≦2 sec | 3 |
| Right hindlimb placing test (leg hanging) | >8 sec | >6 sec | >4 sec | >2 sec | ≦2 sec | 3 |
| Left forelimb placing test (leg hanging) | >8 sec | >6 sec | >4 sec | >2 sec | ≦2 sec | 3 |
| Left hindlimb placing test (leg hanging) | >8 sec | >6 sec | >4 sec | >2 sec | ≦2 sec | 3 |
| Posture | Falling down on the left | Falling to the left | Falling slightly | Normal | | 4 |

TABLE 1-continued

Scale for Evaluation of Neurologic Symptoms

| Test | Score | | | | | Ref. |
|---|---|---|---|---|---|---|
| | 0 | 1 | 2 | 3 | 4 | |
| Resistance to lateral push | No resistance to the right push | Decreased resistance to the right push | Symmetrical response | | | 5 |

Reference 1, Relton et al. (1997); 2, Garcia et al. (1995); 3, Tupper et al. (1980); 4, Longa et al. (1989); 5, Bederson et al. (1986).

5) Data Analysis

The following three exclusion criteria were provided for final analysis, and individuals satisfying the criteria were not used for data analysis.

1̂ The score of neurologic symptoms 60 minutes after initiation of ischemia was 13 points or less (severe) or 17 points or more (mild). No individuals showed a severe state of 12 points or less.

2̂ Failure in the insertion of the plug (After brain isolation, the bottom of the brain was observed. The tip of the plug did not reach the point of origin of MCA, or reached close to the anterior communicating artery.)

3̂ A bypass was present between the internal carotid artery and MCA, making blockage of the bloodstream in MCA by the plug insufficient.

As a result of exclusion, 14 cases in each group were adopted. The results were all shown as the means±standard deviations. Significant differences from the control group were detected by Mann-Whitney test. The significance level was set at 5%.

3. Results

1) Effect of Reducing Infarct Size and Abating Cerebral Edema

The percent cerebral infarction volume for the entire cerebrum was significantly smaller in the KP-102 group than in the control group (FIG. 1). For each of the medulla and the cortex, the effect of shrinking the infarct was observed in the KP-102 group (FIG. 1). The sizes of the cerebral infarcts in the entire cerebrum, the cortex and the medulla were expressed as percentages of the normal hemisphere volume. The asterisks (*) in FIG. 1 mean significant differences (P<0.05) on Mann-Whitney test.

Figure 2:
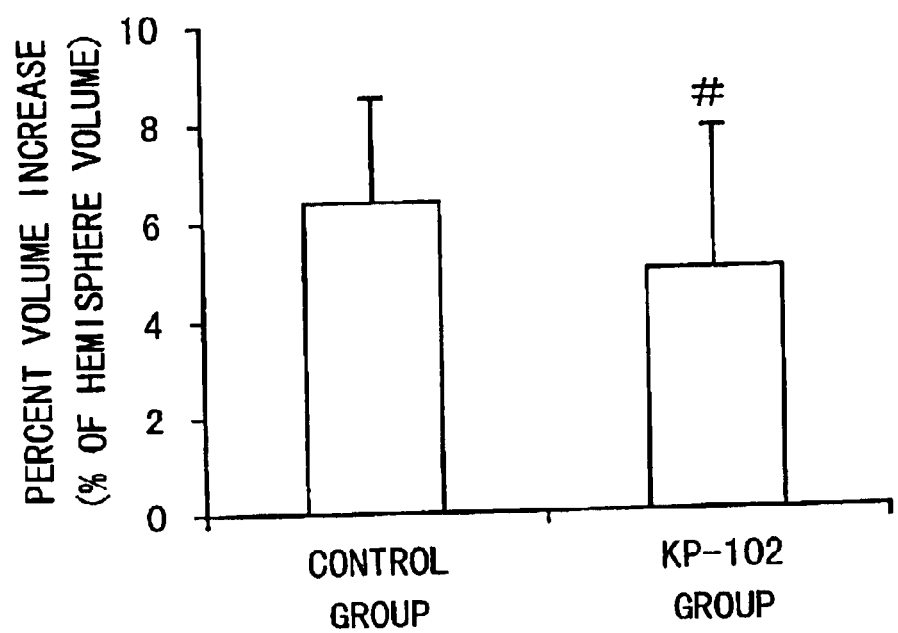
FIG. 2 is a view showing the effect of KP-102 on diminution of cerebral edema in cerebral ischemia-reperfusion models.

Comparisons of the percent edema showed no significant differences, but indicated a tendency toward suppression in the KP-102 group (FIG. 2). The increase in the infarction volume was expressed as a percentage of the volume of the normal hemisphere. The symbol # in FIG. 2 represents a tendency toward improvement (P=0.087) in KP-102 on Mann-Whitney test.

2) Action of Ameliorating Neurologic Symptoms

Figure 3:
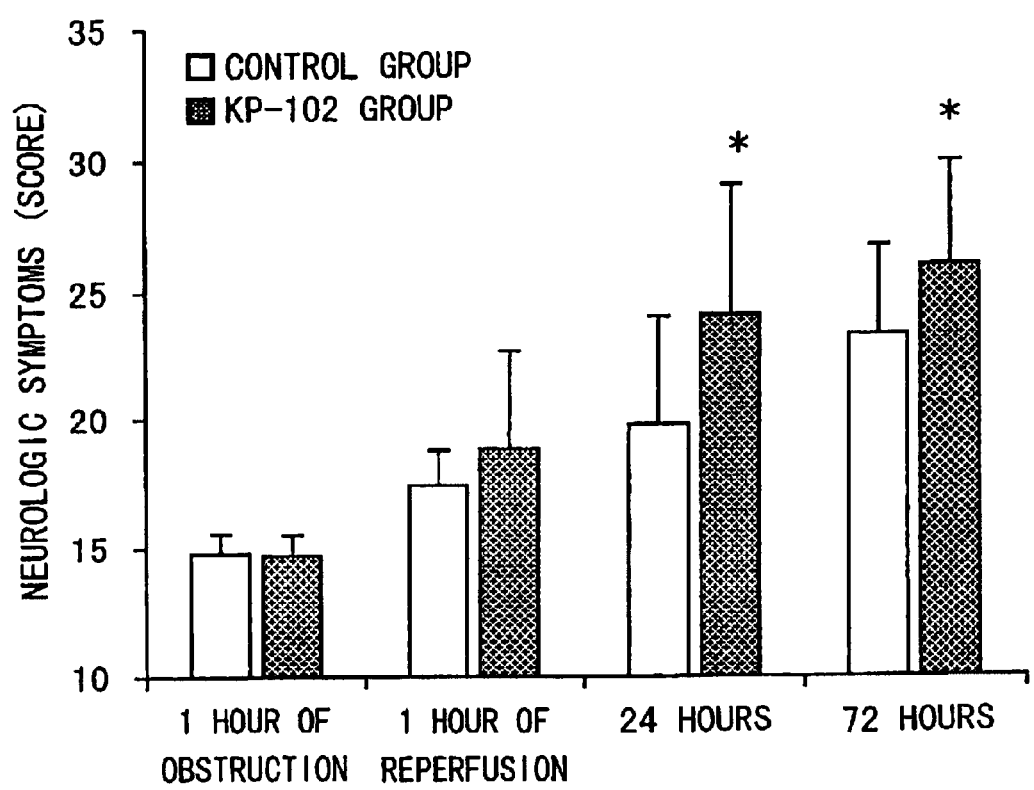
FIG. 3 is a view showing the effect of KP-102 on alleviation of neurologic symptoms in cerebral ischemia-reperfusion models.

Hemiplegia of the left foreleg and the left hind leg observed during ischemia gradually subsided after reperfusion, but persisted even after 72 hours of reperfusion. The score in the KP-102 group was significantly higher than in the control group, showing faster recovery (FIG. 3). The asterisks (*) in FIG. 3 mean significant differences (P<0.05) on Mann-Whitney test.

3) Changes in Body Temperature

The body temperature rose owing to ischemia, and rises up to nearly 40° C. were observed 75 minutes after initiation of ischemia. Then, the elevated temperatures returned to the normal temperature as a result of reperfusion. These changes in body temperature were practically the same in the control group and the KP-102 group (Table 2).

TABLE 2

Changes in body temperature (rectal temperature)

| | Body temperature (° C.) | | | |
|---|---|---|---|---|
| | Immediately before reperfusion | 1 hour of reperfusion | 24 hours of reperfusion | 72 hours of reperfusion |
| Control group | 39.5 ± 0.5 | 37.6 ± 0.5 | 38.1 ± 0.6 | 38.2 ± 0.6 |
| KP-102 group | 39.4 ± 0.3 | 37.3 ± 0.4 | 38.1 ± 0.4 | 38.1 ± 0.5 |

Means ± standard deviations (14 rats/group)

4. Discussion

KP-102, intravenously administered for 3 hours, beginning 30 minutes after initiation of ischemia, decreased the size of the infarct 3 days after reperfusion, abated edema and ameliorated neurologic symptoms, without affecting the body temperature. KP-102 does not influence blood pressure or heart rate. These results show that the growth hormone secretion promoting substance acts to protect against the death of nerve cells brought about by ischemia or ischemia-reperfusion. Hence, it has been found that the growth hormone secretion promoting substance is useful as an agent for prevention or treatment of diseases involving degeneration or death of nerve cells, such as cerebral ischemia, cerebral infarction and cerebral edema.

Test Example 2

Direct Inhibitory Effect of Growth Hormone Secretion Promoting Substance on Death of Nerve Cells 1. Materials KP-102, hexarelin, and non-peptide compounds, i.e., ibutamorelin methanesulfonate (hereinafter referred to as MK-0677) (synthetic product), S-37555, S-38855 and S-39100 {produced by the method described in the publication WO99/09991 (S-37555: compound of Example 160 in the publication), and produced by the method described in the publication WO00/48623 (S-38855 and S-39100: compounds of Examples 4 and 25 in the publication); all these compounds were used as hydrochlorides; details of the compounds are described there}, were each dissolved in dimethyl sulfoxide (Nacalai tesque). The solution was used after dilution to predetermined concentrations with distilled water for injection (JP, Otsuka Pharmaceutical) containing 1 mg/mL of bovine serum albumin (SIGMA). Rat type ghrelin (Peptide Institute) was used after dilution to predetermined concentrations with water for injection containing 1 mg/mL of bovine serum albumin. Other reagents used were L-15 culture medium, D-MEM/F-12 culture medium, MEM culture medium, Neuro Basal culture medium, B-27 supplement, horse serum, newborn calf serum, L-glutamine (all of the foregoing products of GIBCO), L-cysteine, ionomycin, calf serum albumin, DNase I (all of the foregoing products of SIGMA), glucose, viable cell count determination reagent SF (all of the foregoing products of Nacalai tesque), and papain (Worthington Biochemical).

Animals used were fetal rats on the 20th fetal day gestated in Wistar/ST definitively pregnant rats (15–18 days pregnant, Japan SLC).

2. Methods

1) Cultivation of Rat Hippocampal Nerve Cells

Rat hippocampal nerve cells were isolated in accordance with the method of Hatanaka et al. (Hatanaka, H. and Tsukui, H., Dev. Brain. Res. 30(1986)47). Brains were removed from Wistar/ST fetal rats (20 fetal days), and soaked in cold L-15 medium. The meninges were ablated under microscope, and the hippocampus was cut out. Hippocampal tissue was transferred into a test tube containing the L-15 medium, and the test tube was centrifuged for 3 minutes at 700 rpm. Then, the supernatant was removed, and phosphate buffer (pH 7.2) containing papain (0.5 mg/mL), bovine serum albumin (0.2 mg/mL), cysteine (0.2 mg/mL), glucose (5 mg/mL) and DNase I (0.01%) was added, followed by incubating the mixture for 15 minutes at 37° C. Then, horse serum was added, and the mixture was centrifuged for 3 minutes at 700 rpm. Then, the supernatant was removed, D-MEM/F-12 medium was added, and the cells were dispersed by pipetting. After centrifugation for 5 minutes at 700 rpm, the dispersed cells were redispersed in D-MEM/F-12 medium containing 5% newborn calf serum and 5% horse serum, and inoculated in a polyethyleneimine-coated 48-well culture plate (Nunc) at a rate of $4 \times 10^5$ cells/cm$^2$. The cells were cultured in a culture incubator (37° C., 5% $CO_2$-95% air). On the 2nd day of culturing, the culture medium was replaced by Neuro Basal medium containing 2 mM of glutamine and B-27 supplement. Then, the medium was replaced at intervals of 4 days.

2) Induction of Cell Death

Cells on the 14th day of culturing were used in experiments. The culture medium was replaced by a B-27-free MEM medium, and the cells were incubated for 30 minutes. Then, a solvent (dimethyl sulfoxide) and a test compound were added, and the system was incubated for 30 minutes (procedure 1). Then, 3 $\mu$M of ionomycin was added, and the mixture was incubated for 30 minutes (procedure 2). The culture medium was washed, and replaced by Neuro Basal medium containing B-27 supplement, and the system was cultured for 18 hours (procedure 3). In examining the effect of post-treatment, the solvent and the test compound were not added in procedure 1, but added 30 minutes after replacement of the medium in procedure 3.

The viable cell count was determined quantitatively by measuring the absorbance (450 nm) of water-soluble formazan, which was formed by the reductive action of an intracellular dehydrogenase, with the use of the viable cell count determination reagent WST-8 (2-(2-methoxy-4-nitrophenyl)-3-(4-nitrophenyl)-5-(2,4-disulfophenyl)2H-tetrazolium monohydrochloride) as a substrate.

3) Calculation of the Cell Survival Rate

Based on the absorbances obtained, the survival rate was calculated from the following equation, with the cell survival rate for the ionomycin-untreated group as 100%:

Survival rate (%)=(absorbance for test compound·ionomycin treatment−blank absorbance)/(absorbance for solvent·ionomycin non-treatment−blank absorbance)×100

Each treatment was performed in 4 wells/group, and the results were expressed as means±standard deviations. Statistical analysis was made by conducting one-way layout ANOVA, and then performing Dunnett's test for significant differences from the solvent-ionomycin treated group. The symbols * and ** represent significant differences ($p<0.05$ and $p<0.01$, respectively) from the solvent.

3. Results and Discussion

Figure 4:
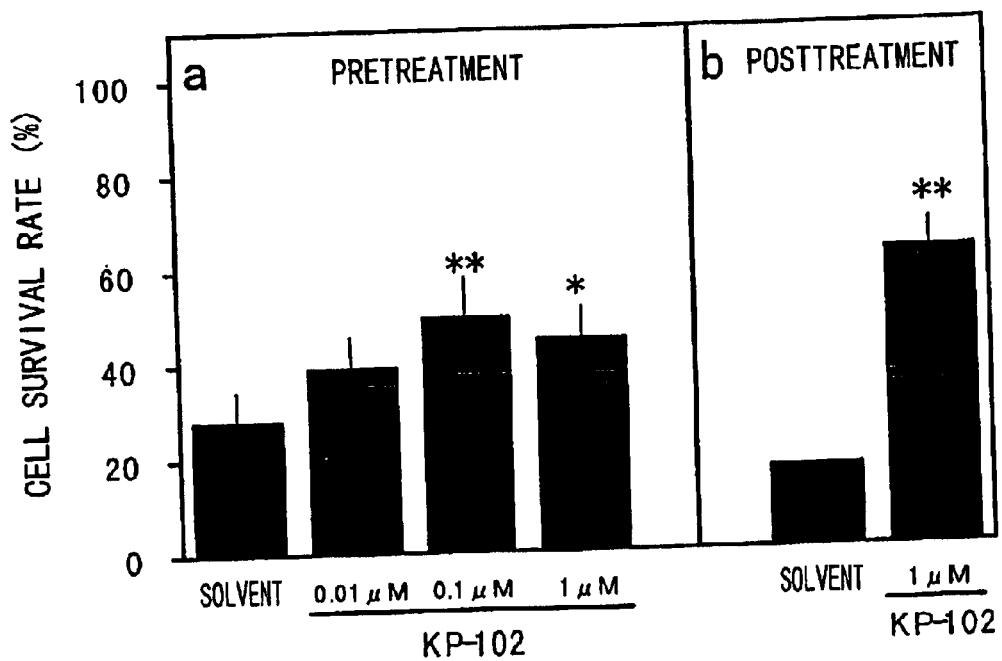
FIG. 4a is a view showing the suppressive effect of KP-102 on death of nerve cells when KP-102 was applied 30 minutes before addition of ionomycin.
FIG. 4b is a view showing the suppressive effect of KP-102 on death of nerve cells when KP-102 was applied 30 minutes after replacement of an ionomycin-treated culture medium.
Figure 5:
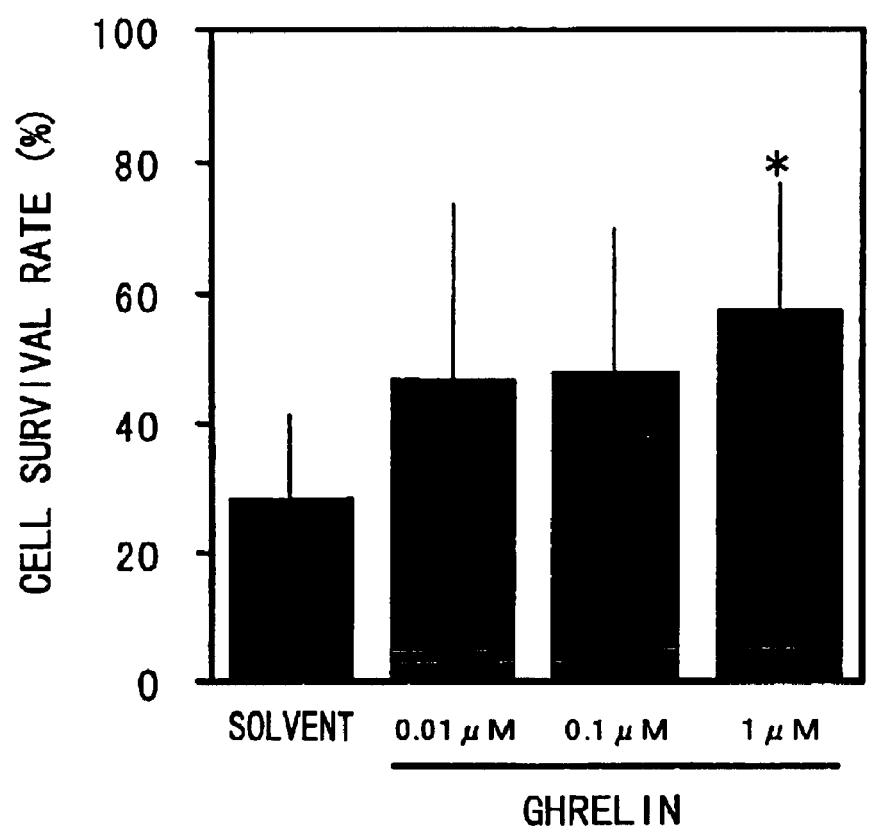
FIG. 5 is a view showing the suppressive effect of ghrelin on death of nerve cells.
Figure 6:
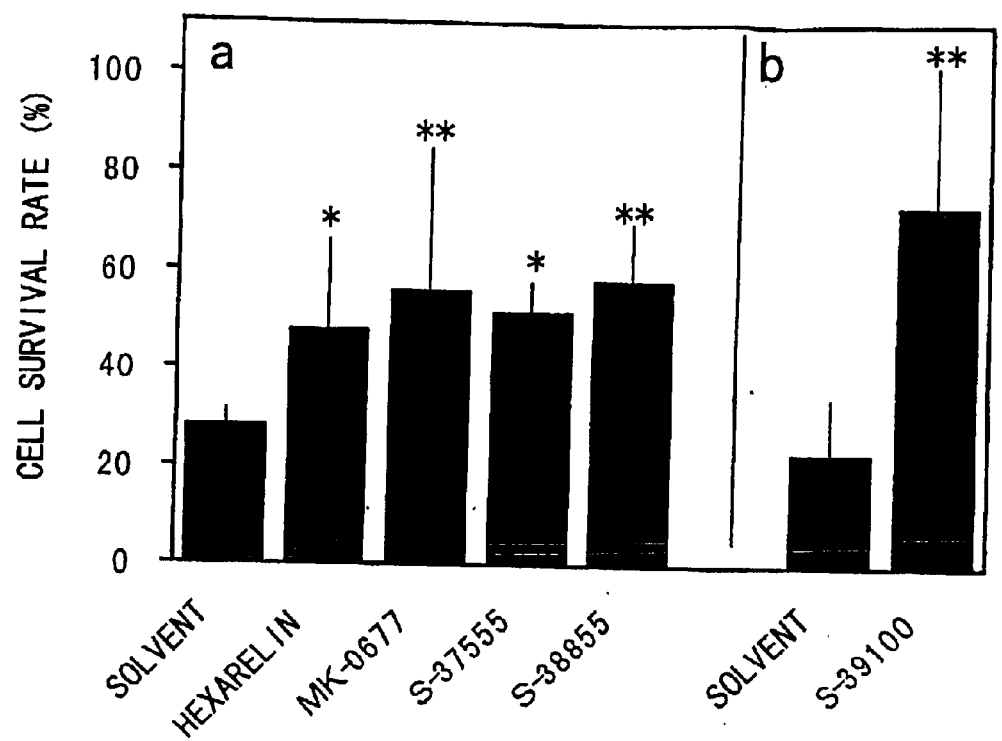
FIG. 6 is a view showing the suppressive effect of hexarelin, MK-0677, S-37555, S-38855 and S-39100 on death of nerve cells.

KP-102 inhibited cell death, which is induced by 3 $\mu$M of ionomycin, dose-dependently at concentrations of 0.01 to 1 $\mu$M (FIG. 4a). This cell death inhibiting action was also confirmed when KP-102 was applied after ionomycin treatment (FIG. 4b). A similar dose-dependent inhibitory action was confirmed for ghrelin (FIG. 5). Further, hexarelin, MK-0677, S-37555, S-38855 and S-39100 (each 0.1 $\mu$M) all showed a clear action of inhibiting cell death (FIGS. 6a and 6b).

Apoptosis-like cell death of a neuron by ionomycin known as an intracellular $Ca^{2+}$ increasing agent is known as a model of a neuronal death associated with various cerebral diseases involving degeneration or death of nerve cells (Takei, N and Endo, Y, Brain Res. 652(1994)65). The present Test Example demonstrated that ghrelin, which is an endogenous growth hormone releasing peptide, KP-102 and hexarelin, which are growth hormone releasing peptides, and MK-0677, S-37555, S-38855 and S-39100, which are non-peptide compounds, all inhibit the death of nerve cells, and thus the growth hormone secretion promoting substances show a protective action on nerve cells.

Hence, an agent for prevention or treatment, containing the growth hormone secretion promoting substance of the present invention as an active ingredient, is effective as an agent for protecting nerves and for preventing or treating diseases involving degeneration or death of nerve cells.

What is claimed is:

1. A method for treating diseases involving degeneration or death of nerve cells or lowering the incidance of death of neurons caused by said diseases characterized by administering a pharmacologically effective amount of a growth hormone secretion promoting peptide or secretagogue to a mammal including a human.

2. The method of claim 1, wherein the diseases are diseases involving ischemic degeneration or death of nerve cells.

3. The method of claim 1, wherein the diseases are cerebrovascular disorders.

4. The method of claim 1, wherein the diseases are cerebral infarction.

5. The method of claim 1, wherein the diseases are cerebral edema.

6. A method for treating nerve cells in a human subject comprising administering an effective amount of an agent containing a growth hormone secretion promoting peptide or secretagogue as an active ingredient to lower the incidance of death of nerve cells caused by diseases including degeneration or death of said nerve cells.

7. The method of claim 6, wherein the death or inhibition of the nerve cells is caused by ischemia or ischemia-reperfusion.

8. The method of claim 7, wherein the method is useful in treating cerebral ischemia, cerebral infarction and cerebral edema.

9. The method of claim 6, wherein the degeneration or death of nerve cells is a cerebral disease.

10. The method of claim 6, wherein the agent contains as an active ingredient a growth hormone releasing peptide or salt or ester thereof.

11. The method of claim 10, wherein the growth hormone releasing peptide or salt or ester thereof is selected from the group consisting of ghrelin, ghrelin analogs, His-D-2-Me-Trp-Ala-Trp-Dphe-Lys-$NH_2$, His-DTrp-Ala-Trp-Dphe-Lys-$NH_2$, DAla-D-2-Nal-Ala-Trp-DPhe-Lys-$NH_2$, Ala-His-D-(2')-Nal-Ala-Trp-DPhe-Lys-$NH_2$,3-(4-Imidazolyl) propionyl-DPhe-Ala-Trp-DPhe ($CH_2NH$)-Lys-NH-ol, 3-Aminomethyl-benzoyl-D-2-Nal-N-Me-Dphe-Lys-$NH_2$, and 2-Me-Ala-His-3-(2-Nal)-DAla-DPhe-Lys-$NH_2$) and salts and esters thereof.

12. The method of claim 1, wherein the mammal is a human.

13. The method of claim 5, wherein the mammal is a human.

14. The method of claim 6, wherein the agent contains as an active ingredient, a GH secretagogue selected from the group consisting of S-38855, S-37555, S-39100, ibutamorelin, capromorelin, NNC-260722, NNC-260323, L-163661, L-163540, L-168721, LY-426410, LY-444711, L-692,429, L-692,585, L-700,653, L-252,564, L-162,752, L-164,080, G-7203, G-7039, G-7052, G-7220, tabimorelin, or salts and esters thereof.

* * * * *